United States Patent [19]

Uhle

[11] 4,171,000
[45] Oct. 16, 1979

[54] SMOKING DEVICE

[76] Inventor: Klaus P. Uhle, Pfitznerstr. 13, D-8070 Ingolstadt, Fed. Rep. of Germany

[21] Appl. No.: 780,539

[22] Filed: Mar. 23, 1977

[51] Int. Cl.² ........................................... A24F 47/00
[52] U.S. Cl. .............................. 131/170 A; 128/203; 128/204; 128/210; 128/211
[58] Field of Search ............... 128/197, 201, 203, 204, 128/208–211; 131/170 R, 170 A, 171 R, 171 A, 10 A, 8 A

[56] References Cited

U.S. PATENT DOCUMENTS

| 2,830,597 | 4/1958 | Kummli | 131/170 A X |
| 3,721,240 | 3/1973 | Tomburi | 128/208 |

Primary Examiner—Robert W. Michell
Assistant Examiner—V. Millin
Attorney, Agent, or Firm—Gilbert L. Wells; Heinrich W. Herzfeld

[57] ABSTRACT

A smoking device for aspirating gas-containing mixtures is described which comprises a mouthpiece with at least one suction duct connected to an intermediate chamber, a pressure vessel filled with a mixture disposed next to the intermediate chamber and including an outlet valve that is closed in normal position and ends into the intermediate chamber and has to be opened to put the device into operation, and further comprising an inlet for atmospheric air into the intermediate chamber which is provided with a shut-off valve coupled to the outlet valve, wherein the shut-off valve is open in the normal position and can be brought into closing position when the outlet valve normally urged into closing position is opened, and that the intermediate chamber contains a storage substance for storing the gas-containing mixture.

9 Claims, 1 Drawing Figure

U.S. Patent    Oct. 16, 1979    4,171,000
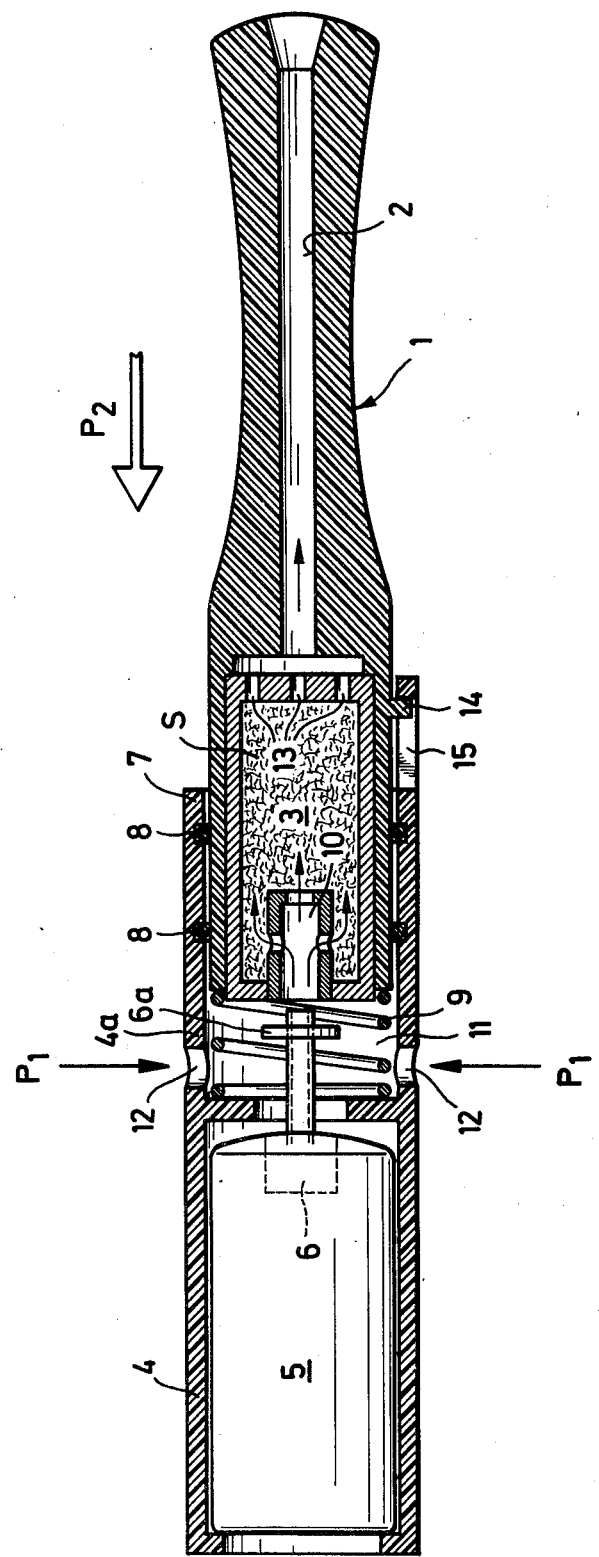

SMOKING DEVICE

BACKGROUND OF THE INVENTION

The invention relates to a smoking device for aspirating gascontaining mixtures comprising a mouthpiece with at least one suction duct and which is connected to an intermediate chamber, a pressure vessel filled with the mixture disposed next to the intermediate chamber and including an outlet valve which is closed when the device in inoperative rest position and opens into the intermediate chamber and has to be opened to put the device into operation, and further comprising an inlet for atmospheric air into the intermediate chamber which inlet is provided with a shut-off valve coupled to the outlet valve.

Smoking devices for aspirating gas-containing mixtures comprising a mouthpiece with a suction duct and a means for holding a source of a mixture have been known which include an intermediate chamber with an inlet and an outlet between the holding means and the suction duct.

Smoking devices of the type mentioned above have been known in manifold embodiments as cigar or cigarette holders. In said devices the intermediate chamber contains an adsorbent for the harmful components of tobacco smoke, such as nicotine or tar products.

Such a device has been known from U.S. Pat. No. 3,721,240.

OBJECT AND SUMMARY OF THE INVENTION

It is an object of the invention to provide a smoking or aspirating device which is designed to receive, in lieu of a cigarette or cigar as a source of mixture, another source of mixture which contains substances completely different from tobacco or tobacco products and which may contain, for instance, harmless pleasantly flavored or even health-promoting components. The purpose of this is to gradually wean the user addicted to the consumption of tobacco products from such consumption.

This object is achieved, according to the invention, by an improvement of a smoking device of the type initially described wherein the shut-off valve of the atmospheric air inlet opening into the intermediate chamber is open with the device is in rest position, that on the other hand the shut-off valve may be brought into closed position is opened, and that the intermediate chamber contains a substance for holding the gas-containing mixture in storage, preferably an absorptive material.

The pressure vessel disposed next to the intermediate chamber of the device of the invention may contain as mixture various flavors, e.g. eucalyptus, peppermint, orange, lemon flavor, etc. The flavors may be mild, sour, acid etc. Moreover, it is possible to admix health-promoting agents, e.g. agents preventing tooth or gum diseases such as caries and parodontosis or the like. Furthermore, it is possible to include in the mixture of the pressure vessel preparations suited for inhalation, e.g. preparations having therapeutical activity.

The use of the device of the invention is very simple. It is only necessary to move the intermediate chamber toward the outlet valve of the pressure vessel until the said valve opens. After a short time during which the mixture flows from the source, i.e. from the pressure vessel, into the intermediate chamber the storing substance of the intermediate chamber is charged, whereafter the latter can be restored to its rest position. Now it is possible to aspirate a certain number of drafts from the intermediate chamber until its contents are exhausted. Thereafter the storing substance in the intermediate chamber can be recharged from the pressure vessel.

According to a further embodiment of the invention, the intermediate chamber with its inlet and the pressure vessel with its outlet valve may be coaxially aligned with one another whereby the device of the invention may be produced largely analogously to cigarette or cigar holders.

Furthermore, the mouthpiece which preferably is devised to accommodate the intermediate chamber may be engaged gas-tight with a sleeve accommodating the pressure vessel and may be urged away from the pressure vessel with in rest position. This measure has the result that after recharging of the storage substance in the intermediate chamber the device will automatically return into its rest position.

This embodiment may be especially favorably modified by providing a coil spring between the mouthpiece and the sleeve.

In a further embodiment of the invention the sleeve may overlap a portion of the mouthpiece, and at least one sealing ring is provided in said portion. This ensures that during recharging of the storage substance the intermediate chamber will be largely sealed against infiltration of air.

According to still another embodiment of the invention, it is possible to form an air aspirating chamber between the pressure vessel and the intermediate chamber; said air aspirating chamber is radially confined by the sleeve which has at least one air passage in the region of the air aspirating chamber. The latter is hermetically sealed against ambient air while the storage substance is being charged with gas containing mixture.

Preferably the coil spring serving to bias the mouthpiece is arranged within the region of the air aspirating chamber. This offers an especially favorable constructional solution. According to a further modification of the invention, the sleeve and the mouthpiece are threaded engaged with one another, so that movement of the intermediate chamber from the normal position to the charging position and back is possible without the use of a coil spring. This permits even safer operation of the device of the invention.

Incidentally, it is especially advantageous to provide for replacement of an empty pressure vessel by a new vessel filled with the mixture.

BRIEF DESCRIPTION OF THE DRAWING

Hereafter the invention will be explained in more detail with reference to the drawing which illustrates a preferred embodiment of a smoking device of the invention in normal position, in axial sectional view.

DETAILED DESCRIPTION OF THE PREFERRED EMBODIMENT

The illustrated device comprises a mouthpiece 1 with a suction duct 2 having its end remote from the mouth designed for accommodating an intermediate chamber 3 filled with a storage substance S.

A sleeve 4 receives in its interior a pressure vessel 5 which is sealed in an manner known per se by a valve 6 and is maintained under propellant gas pressure. The pressure vessel 5 contains a mixture of flavoring substances thereby forming a source for a gascontaining mixture. A portion 7 of the sleeve 4 overlaps a portion of the mouthpiece 1; in the latter portion two O-rings 8 are inserted. Between the mouthpiece 1 and the sleeve 4 a coil spring 9 is provided such that the mouthpiece 1 is in gas-tight engagement with the sleeve 4 and is urged away from the pressure vessel 5. Through structural elements 14 and 15 the mouthpiece is engaged with or locked to the sleeve 4 or the portion 7 thereof to perdetermine the maximum distance between the intermediate chamber 3 and the pressure vessel 5.

The inlet 10 into the intermediate chamber 3 is axially aligned with the valve 6 of the pressure vessel 5. In the region of the coiled spring 9 an air aspirating chamber 11 with a plurality of air inlets 12 is formed by the adjacent part 4a of the sleeve 4 to admit air therein to flowing in the direction of arrows P1. The entry of air is not obstructed by the coiled spring 9 which is provided in the region of the air aspirating chamber 11.

In order to put the device in operation, the mouthpiece 1 together with the intermediate chamber 3 is moved axially in the portion 7 of the sleeve 4 in the direction of the arrow P2 against the biasing force of the coiled spring 9 to first bring the inlet 10 of the intermediate chamber 3 into gas-tight contact with the valve 6 which will open upon continued axial movement, whereby mixture maintained under propellant gas pressure will flow from the pressure vessel 5 into the intermediate chamber 3, as indicated by the three arrows (not provided with numerals) at the inlet 10. When the pressure upon sleeve 4 and the mouthpiece 1 toward each other ceases, the device will return to its rest position illustrated in the drawing under the influence of the coiled spring 9. Thereafter, when suction is applied to the suction duct 2 of the mouthpiece 1, air will flow into the air aspirating chamber 11 in the direction of arrows P1 and thence through the inlet 10 into the intermediate chamber 3 wherein the mixture stored in the chamber is released into the air flowing therethrough. The air laden with the mixture will flow outlets 13 of the intermediate chamber 3 into the suction duct 2. According to a modification not shown the end of the mouthpiece 1 surrounding the intermediate chamber 3 may be provided with a threading to engage a corresponding threading of the portion 7 of the sleeve 4.

What is claimed is:

1. A smoking device for aspirating a gas-containing mixture comprising a mouthpiece with at least one suction duct connected to an air-aspirating chamber, a pressure vessel filled with said mixture attached to said air-aspirating chamber and including an outlet valve being biased into closed position and connected to said air-aspirating chamber which outlet valve has to be opened to put the device into operation, an inlet for atmospheric air into said air-aspirating chamber which is provided with a shut-off valve coupled to the outlet valve, means for biasing said shut-off valve into open position and means for bringing said shut-off valve into closing position and opening said outlet valve and further comprising an intermediate chamber containing a storage substance for storing said gas-containing mixture, said intermediate chamber being disposed between said air-aspirating chamber and said mouthpiece.

2. The device of claim 1, wherein said intermediate chamber with its inlet and the pressure vessel with its valve are axially aligned.

3. The device of claim 2, wherein said mouthpiece is constructed to accommodate said intermediate chamber in gas-tight engagement with a sleeve accommodating said pressure vessel and said mouthpiece is biased away from said pressure vessel.

4. The device of claim 3, wherein a coiled spring is provided between said mouthpiece and said sleeve.

5. The device of claim 4, wherein said sleeve overlaps a portion of said mouthpiece, and in said portion at least one sealing ring is provided.

6. The device of claim 5, wherein said air-aspirating chamber is radially confined by said sleeve, and that said sleeve has at least one air passage in the region of said air-aspirating chamber.

7. The device of claim 6, wherein said coiled spring is provided in the region of said aspirating chamber.

8. The device of claim 7, wherein said sleeve and said mouthpiece are threadably engaged.

9. The device of claim 1, wherein said pressure vessel is exchangeable.

* * * * *